United States Patent
Rhodes et al.

(10) Patent No.: US 9,304,112 B2
(45) Date of Patent: Apr. 5, 2016

(54) METHOD FOR DETECTING THE PURITY OF GOLD BULLION

(71) Applicants: George Wyatt Rhodes, Corrales, NM (US); Sara Vollmert Rhodes, Corrales, NM (US)

(72) Inventors: George Wyatt Rhodes, Corrales, NM (US); Sara Vollmert Rhodes, Corrales, NM (US)

( * ) Notice: Subject to any disclaimer, the term of this patent is extended or adjusted under 35 U.S.C. 154(b) by 193 days.

(21) Appl. No.: 13/857,667

(22) Filed: Apr. 5, 2013

(65) Prior Publication Data

US 2014/0298911 A1   Oct. 9, 2014

(51) Int. Cl.
  *G01N 29/12*   (2006.01)
  *G01N 29/44*   (2006.01)
  *G01N 33/20*   (2006.01)

(52) U.S. Cl.
  CPC .......... *G01N 29/12* (2013.01); *G01N 29/4427* (2013.01); *G01N 33/20* (2013.01); *G01N 2291/0234* (2013.01)

(58) Field of Classification Search
  CPC ............. G01N 29/12; G01N 29/4427; G01N 2291/0234; G01N 33/20
  USPC .................................................. 73/579, 659
  See application file for complete search history.

(56) References Cited

U.S. PATENT DOCUMENTS

| | | | | |
|---|---|---|---|---|
| 5,062,296 A | * | 11/1991 | Migliori | 73/579 |
| 5,351,543 A | * | 10/1994 | Migliori et al. | 73/579 |
| 5,408,880 A | * | 4/1995 | Rhodes et al. | 73/579 |
| 5,591,913 A | * | 1/1997 | Tucker | 73/628 |
| 5,992,234 A | * | 11/1999 | Rhodes et al. | 73/579 |
| 6,684,701 B2 | * | 2/2004 | Dubois et al. | 73/579 |
| 8,903,675 B2 | * | 12/2014 | Jauriqui et al. | 702/124 |

FOREIGN PATENT DOCUMENTS

JP   58155335   *   9/1983

* cited by examiner

*Primary Examiner* — J M Saint Surin

(57) ABSTRACT

The density of gold and tungsten are almost identical, allowing for substitution by unscrupulous entities. The detection of the replacement is difficult to detect by common nondestructive testing methods, and repositories have resorted to drilling, cutting and melting samples of gold bars to certify their integrity. Resonant ultrasound spectroscopy allows a digital fingerprint to be produced, which has been shown to be effective in the detection of tampering. These spectra are representative of the dimensions, density and elastic constants of any solid object. Since the dimensions and density are essentially identical for pure and adulterated gold samples, only the elastic constant variance changes the spectral fingerprint. The method described in this application provides a reliable and accurate process to certify the integrity of gold samples.

4 Claims, 3 Drawing Sheets

|  | Density (g/cm3) | Young's Modulus (GPa) |
|---|---|---|
| Gold | 19.30 | 79 |
| Tungsten | 19.25 | 411 |
| Iridium | 22.56 | 528 |

METHOD FOR DETECTING THE PURITY OF GOLD BULLION

This application claims the benefit of priority of U.S. Provisional Applications No. 61/640,847, filed May 1, 2012 and No. 61/654,466 filed Jun. 1, 2012.

BACKGROUND

1. Field of the Invention

This invention relates to the nondestructive testing of gold pieces (bullion, bars coins . . . ) to ensure they contain only gold and have not been subject to dissimilar metal substitution.

2. Brief Description of the Related Art

Reports indicating that gold bullion is being physically hollowed and replaced with similar density metals, such as tungsten, are surfacing. While not a huge concern for the original manufacturer, the secondary exchange market can experience disruption if the integrity of the asset comes into question. Verifying the sample purity is critical and must be performed quickly, and nondestructively. Several potential test methods are applicable, but most are not good solutions for expense and technical reasons.

In physics, resonance is the tendency of a system to oscillate at a greater amplitude at some frequencies than at others. These are known as the system's resonant frequencies (or resonance frequencies) and are generally functions of the square root of the stiffness over the mass. Since each unique metal has a set of well defined elastic constants, the stiffness of the 2 metals will always be different, meaning that the resonances produced from any driving forces will be different and easily measured. Resonances can be produced from any swept sine spectrometer (preferred) or with an impulse function (striking with a hammer). Independent of how the resonance spectrum is created, it can be measured and compared with known good samples to observed whether or not it has been altered.

U.S. Pat. No. 5,922,956; "Dynamic Ultrasonic Resonant Testing, Rhodes, Jul. 13, 1999, describes a sample being excited by an exciting mechanical input (transducer) at a plurality of ultrasonic frequencies (the swept sine method), and sensing the resonant mechanical responses with the inverse process (1 or 2 mechanical receiving transducers). A dynamic signal analyzer is connected to receive the response of the sample and to output the resonance spectrum. A computer then determines the relevant resonances that adequately describe the conforming spectrum.

U.S. Pat. No. 5,495,763; Rhodes, et al. Mar. 5, 1996 entitled "Method for resonant measurement" first described the relevant resonance response characteristics of a sample being determined for use in characterizing the sample for non-destructive testing. Applying the same method to an adulterated sample, will immediately be obvious as the spectrum will shift according to the elastic property changes and some resonances will show additional differences in splitting and Q (the quality of the resonance as defined as the full width at half maximum), as was this is done by submitting numerous known conforming samples to examination and mapping the resonance responses. The conforming samples will produce a nearly identical spectrum, where nonconforming will show shifts, line splitting and Q differences.

In U.S. Pat. No. 5,062,296, Migliori described resonant ultrasound spectroscopy as a method to provide a unique characterization of an object for use in distinguishing similar objects having physical differences greater than a predetermined tolerance. A resonant response spectrum is obtained for a reference object by placing excitation and detection transducers at any accessible location on the object. The spectrum is analyzed to determine the number of resonant response peaks in a predetermined frequency interval. The distribution of the resonance frequencies is then characterized in a manner effective to form a unique signature of the object. In one characterization, a small frequency interval is defined and stepped though the spectrum frequency range. Subsequent objects are similarly characterized where the characterizations serve as signatures effective to distinguish objects that differ from the reference object by more than the predetermined tolerance.

U.S. Pat. Nos. 5,922,956, 5,495,763 and 5,062,296 are hereby incorporated by reference in their entirety.

SUMMARY

The embodiments disclosed herein relate to the examination of gold pieces using the technology of Resonant Ultrasound Spectroscopy. The resonant frequencies can be driven either by a swept sine oscillator or an impulse function obtained by being stricken with an appropriate solid object. The resulting resonances are detected and displayed to yield a pattern representative of conforming test objects like gold bars, bullion, coins . . . . Pieces found to be nonconforming will be flagged, separated and should be submitted to further testing, including destructive means (melting, cutting and drilling).

The RUS spectrum is created by placing a billet on a fixture containing a transducer that broadcasts a swept sine, ultrasonically driven mechanical excitation to the sample, or by striking the object with a mechanical force (hammer) and one or more identical transducers are used to detect the resonances produced. This process takes a few seconds to yield the signature. While there are hundreds of potential resonances that can be used, it is only useful to observe the absolute frequency, and the line shape Q (full width at half maximum defining Q) of a few resonances to select those which provide the required diagnostic information. Some resonances are associated with geometry, but all are affected by the elastic properties. For example, the substitution of tungsten for gold, although the densities are similar (gold=19.30 g/cm3 and tungsten=19.25 g/cm3), while not easily detected with weight scales, significantly change the elastic properties allowing simple detection. Moreover, it should be noted that gold samples of 400 Troy ounces actually vary from 380 to 420 ounces, according to the Royal Canadian Mint.

The sample geometry should be substantially identical for all test objects to properly establish the baseline from which all samples can be compared. Even with the weight variances addressed above, it is found that the resonance spectra simply move together to higher, or lower, frequencies while maintaining the identical pattern. While geometry is less important than the other factors governing the resonance pattern, the best comparative results will be obtained when the variability is less than a few percent in dimensions including embossed features. Either software, or the system operator may make the judgment whether the sample being examined conforms to the selection criteria, or not.

This invention relates to the creation of resonances by connecting a frequency synthesizer to a piezoelectric material, causing that material to vibrate. The vibrating material (transducer) is placed into contact with the test sample, and the frequency synthesizer is stepped through a variety of frequencies which were previously determined to be in a range where distinct resonances could be observed. The test sample is also in contact with an additional, identical transducer, which senses the induced vibrations (resonances). The resulting signal is amplified and sent to a digital signal processor which may have the ability to examine both the in-phase and quadrature components of the signal. These data are easily processed in a computer to create a display of the resonance pattern.

This invention relates to a method by which the object under test is impacted by a solid object (e.g. a hammer) causing the structure to "ring" like a bell. Similar to the swept sine approach discussed above, an appropriate transducer senses the induced vibrations and through digital processing, and a computer, displays a resonance pattern.

This invention includes a method of examining gold samples to ensure their integrity comprising the steps of:

mounting the gold object to be tested on an appropriate test stand;

contacting the gold sample by a minimum of two identical transducers without allowing any additional contacts that might dampen the resonance to be produced;

creating resonances in the gold sample by either actively vibrating a piezoelectric transducer through a predetermined range of interest, or striking the sample with a solid object to produce resonances;

sensing the resultant resonances with a piezoelectric transducer;

amplifying the transducer signal sufficient to meet signal to noise requirements;

processing, in a computer with appropriate algorithms, the in phase and quadrature components of said resonance signal; and displaying those data in a format where either a system, or human can make a judgment whether the test object has a resonance patter conforming to known "good" samples or not.

Spectra produced by the means described above, can easily be displayed for comparison by the human eye, or a computer algorithm. If an algorithm is used, some method to identify the absolute frequency is desired. There are several mathematical routines available for the purpose that have been applied in many industrial applications, which are not proprietary. Additionally, it is useful to display multiple spectra on a single graph, as is shown in multiple figures in the attached drawings. If the computer must accept, or reject samples based on spectral differences, these algorithms are trivial and easily developed.

DETAILED DESCRIPTION OF EMBODIMENTS

Figure 1:
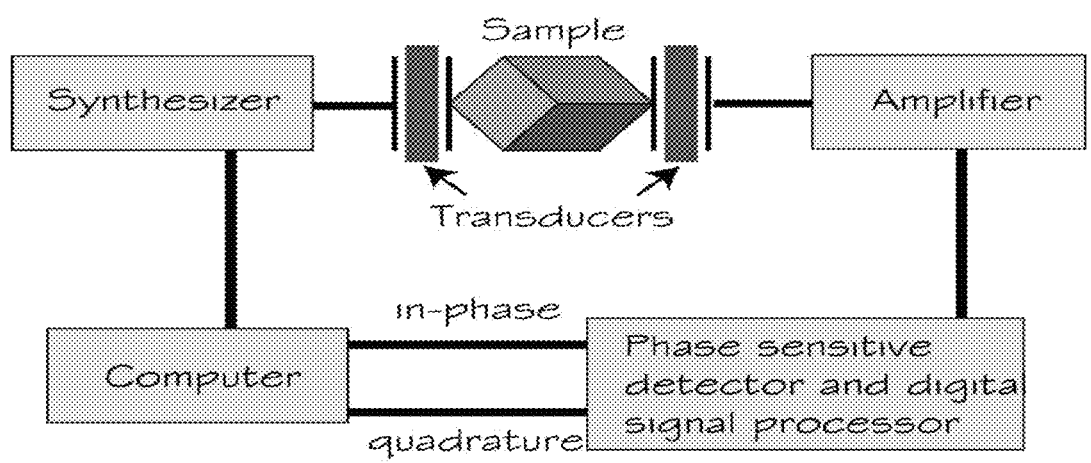
FIG. 1 shows a schematic diagram of a resonant ultrasound spectrometer.

FIG. 1 shows a schematic diagram of a resonant ultrasound spectrometer. In all resonant ultrasound spectrometers a frequency synthesizer produces an electrical signal that is connected to a piezoelectric crystal, converting the electrical signal to a mechanical vibration. This mechanical transducer contacts a part (gold bar) causing it to vibrate. When a natural resonance of the material is found, the vibration occurs throughout the part. An additional transducer (or 2) in contact with the part, sense the mechanical displacement, creating an electrical signal which can be amplified, and processed to yield a display of the spectrum. These mechanical vibrations occur solely due to the dimensions, density and elastic properties of the part. Since the dimensions and density are nearly identical for conforming, and nonconforming (doped with tungsten) changes are associated with a difference in elastic properties.

Figure 2:
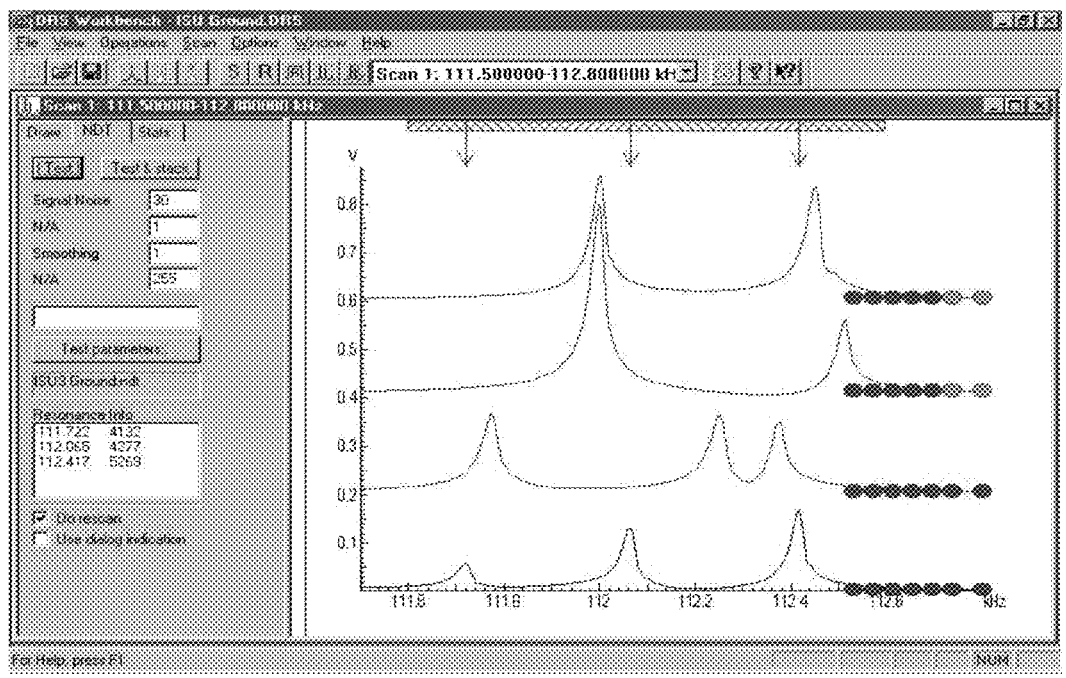
FIG. 2 shows a display of a resonance spectrum where some conforming parts are compared to those known to be nonconforming

FIG. 2 shows comparative spectra for conforming and nonconforming parts. In this example, either the system algorithm, or an operator has the ability to accept, or reject the samples under test.

Figure 3:
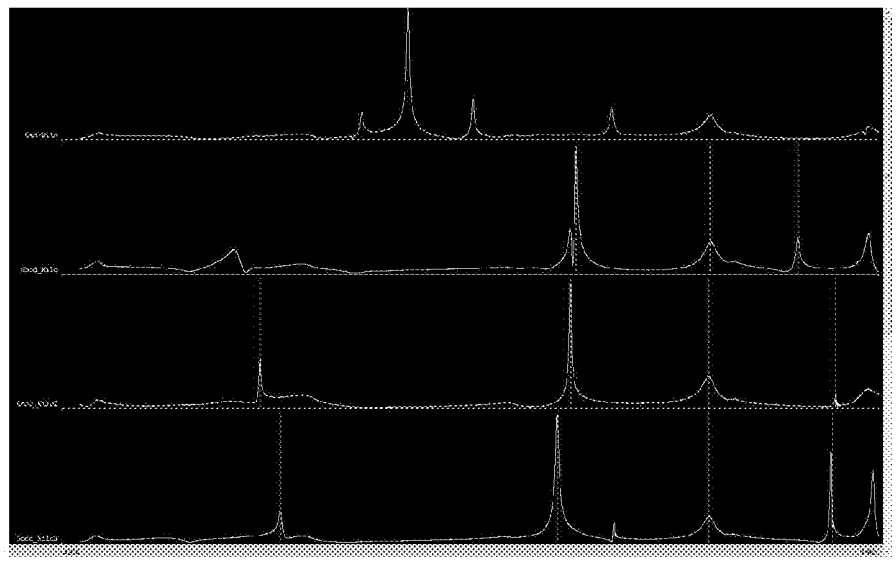
FIG. 3 shows resonant ultrasound spectra for 4, 1 Kg gold bars taken at the Royal Canadian Mint.

FIG. 3 shows comparative spectra for known good and intentionally doped gold bars. These 1 Kg samples were prepared by the Royal Canadian Mint. The top spectrum represents a bar that has been intentionally doped with a small amount of tungsten, while the next three are known good samples.

Figure 4:
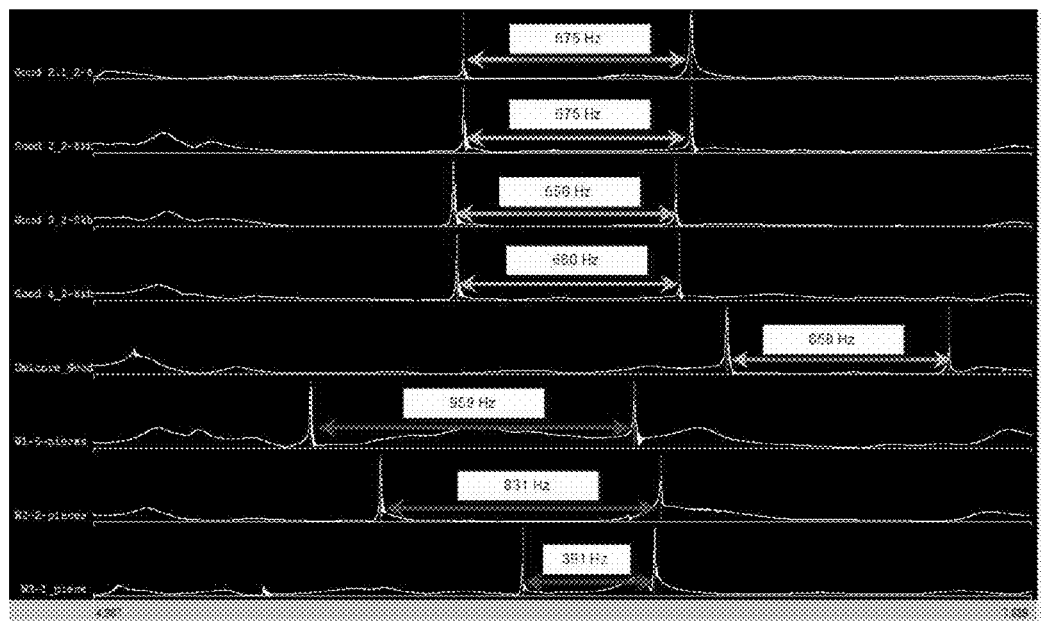
FIG. 4 shows resonant ultrasound spectra for 8, 400 ounce gold bars taken at the Royal Canadian Mint.

FIG. 4 shows multiple 400 ounce bars prepared by the Royal Canadian Mint. The top 5 are conforming and the bottom 3 all have varying amounts of tungsten that has been substituted.

Figures 5, 6:
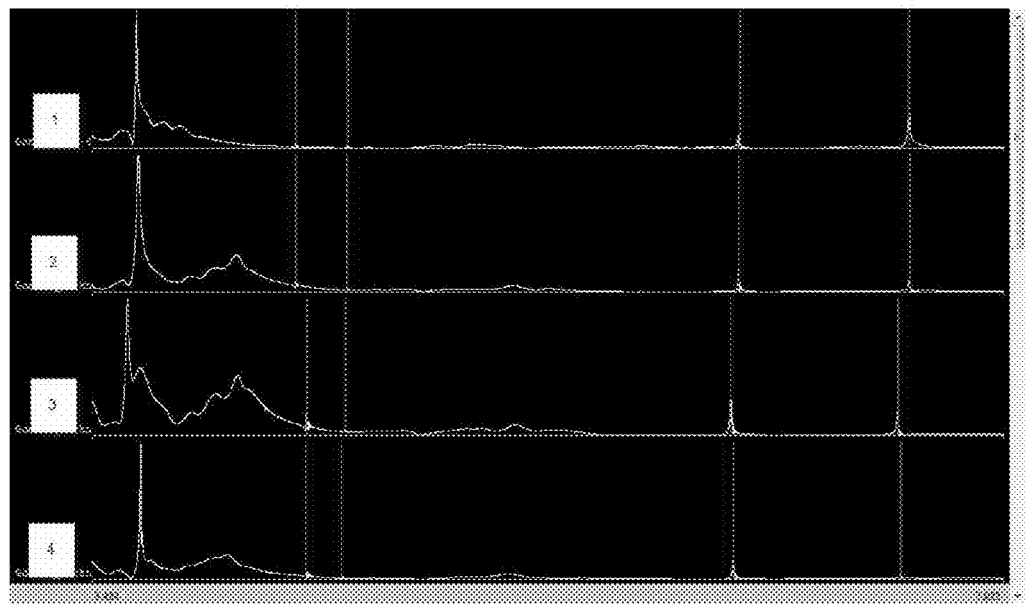
FIG. 5 shows the broad spectra for 4 good 400 ounce gold bars.
FIG. 6 shows the comparison of gold properties with those of tungsten and iridium as potential doping metals.

FIG. 5 illustrates that the spectra are nearly identical for pure gold (99.9995%) despite slight differences in weights and dimensions.

FIG. 6 displays the physical properties affecting resonances of gold, tungsten and iridium.

These spectra clearly show the ability of creating, and analyzing resonant ultrasound spectra to discriminate between conforming and nonconforming gold bars, the latter containing tungsten inserts. It provides the user a quick, and reliable method to verify the integrity of bullion, bars and coins which must be certified to be 99.9999% gold.

While the invention has been described in conjunction with the specific exemplary embodiments thereof, it is evident that many alternatives, modifications, and variations will be apparent to those skilled in the art. Accordingly, embodiments of the invention as set forth herein are intended to be illustrative, not limiting. There are changes that may be made without departing from the spirit and scope of the invention.

What is claimed is:

1. A method of detecting the presence of a first metal inserted into a second metal comprising the steps of:

measuring a second metal baseline object using resonant ultrasound spectroscopy;

measuring an unknown object having similar dimensions, and density as the baseline object using resonant ultrasound spectroscopy;

comparing the baseline object and unknown object resonant ultrasonic spectra to determine if the unknown object has essentially the same resonance structure as the baseline object;

and detecting the presence of the first metal in the unknown object by observing differences in the resonant ultrasound spectra, solely due to elastic property differences in the baseline object and the unknown object.

2. The method in claim 1 where the resonant ultrasound spectrum is created by using a frequency synthesizer as the mechanical driving force.

3. The method in claim 1 where the resonant ultrasound spectrum is created by using an impact device as the mechanical driving force.

4. A method of detecting the presence of tungsten inserted into pure gold bullion comprising the steps of: measuring a gold metal baseline object using resonant ultrasound spectroscopy;
   measuring an unknown object having similar dimensions, and density as the baseline object using resonant ultrasound spectroscopy;
   comparing the pure gold baseline object and unknown object resonant ultrasonic spectra to determine if the unknown object has essentially the same resonance structure as the pure gold baseline object;
   and detecting the presence of the tungsten in the unknown object by observing differences in the resonant ultrasound spectra, solely due to elastic property differences in the baseline object and the unknown object.

\* \* \* \* \*